United States Patent
Yu et al.

(10) Patent No.: US 7,209,782 B2
(45) Date of Patent: Apr. 24, 2007

(54) FULL-RANGE ELECTROTHERAPY UNIT WITH DIGITAL FORCE MODUTATOR

(76) Inventors: Link Yu, No. 90-94, Shang Ta, Shang Ta Village, Kuan Ying Hsiang, Taoyuan Hsien (TW); Ching-Fwu Suen, No. 83, Ta Chiao 5th Street, Yung Kang City, Tainan Hsien (CN)

( * ) Notice: Subject to any disclaimer, the term of this patent is extended or adjusted under 35 U.S.C. 154(b) by 101 days.

(21) Appl. No.: 11/011,286

(22) Filed: Dec. 13, 2004

(65) Prior Publication Data

US 2006/0129208 A1    Jun. 15, 2006

(51) Int. Cl.
*A61N 1/00* (2006.01)
(52) U.S. Cl. .......................................... 607/2
(58) Field of Classification Search ............... 128/901, 128/902, 908; 607/2
See application file for complete search history.

(56) References Cited

U.S. PATENT DOCUMENTS

| | | | | |
|---|---|---|---|---|
| 3,924,641 A | * | 12/1975 | Weiss | 607/74 |
| 4,194,238 A | * | 3/1980 | Masaki et al. | 363/17 |
| 4,890,616 A | * | 1/1990 | Pinckaers | 607/2 |
| 5,036,850 A | * | 8/1991 | Owens | 607/66 |
| 6,249,706 B1 | * | 6/2001 | Sobota et al. | 607/115 |
| 2001/0044640 A1 | * | 11/2001 | Akiyama et al. | 607/2 |
| 2003/0187485 A1 | * | 10/2003 | Sturman et al. | 607/72 |

FOREIGN PATENT DOCUMENTS

JP              63294255 A    * 11/1988

* cited by examiner

*Primary Examiner*—Robert Pezzuto
*Assistant Examiner*—Yun Haeng Lee
(74) *Attorney, Agent, or Firm*—Charles E. Baxley

(57) ABSTRACT

An electrotherapy unit includes a central processor, a digital force modutator connected to and controlled by the central processor, a voltage-increasing transformer, and two conductive pads connected to a secondary coil of the voltage-increasing transformer. The digital force modutator includes two pairs of transistors each having an input side connected to the central processor. The central processor controls conduction/non-conduction of the transistors. A loop for each transistor is connected to the power supply and the primary coil of the voltage-increasing transformer. A diode and a capacitor are connected in parallel between a collector and an emitter of each transistor. The diodes avoid damage to the transistors resulting from an electromotive generated by the primary coil of the voltage-increasing transformer. The capacitors reduce noise signals generated during switching operation of the transistors and the diodes. The capacitors provide bypass for high-frequency noise signals.

5 Claims, 8 Drawing Sheets

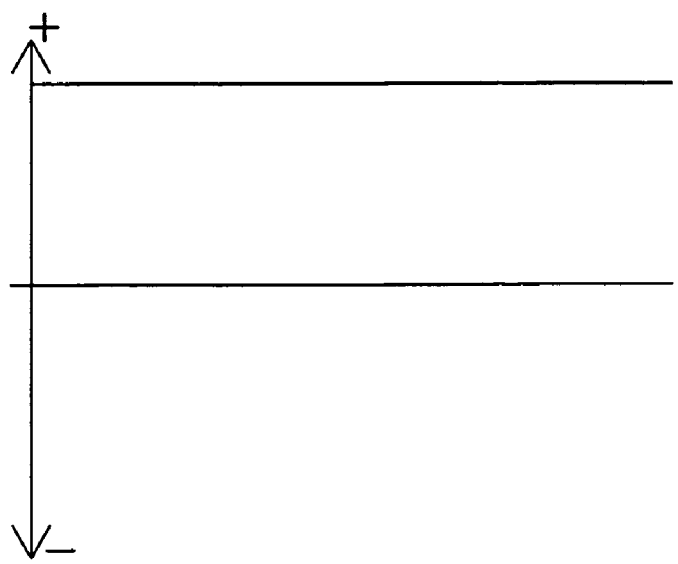
F I G . 5A
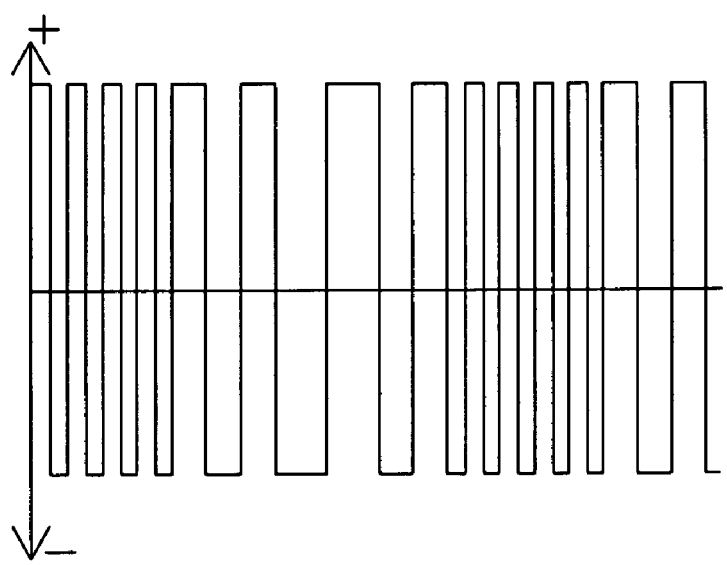
F I G . 5B

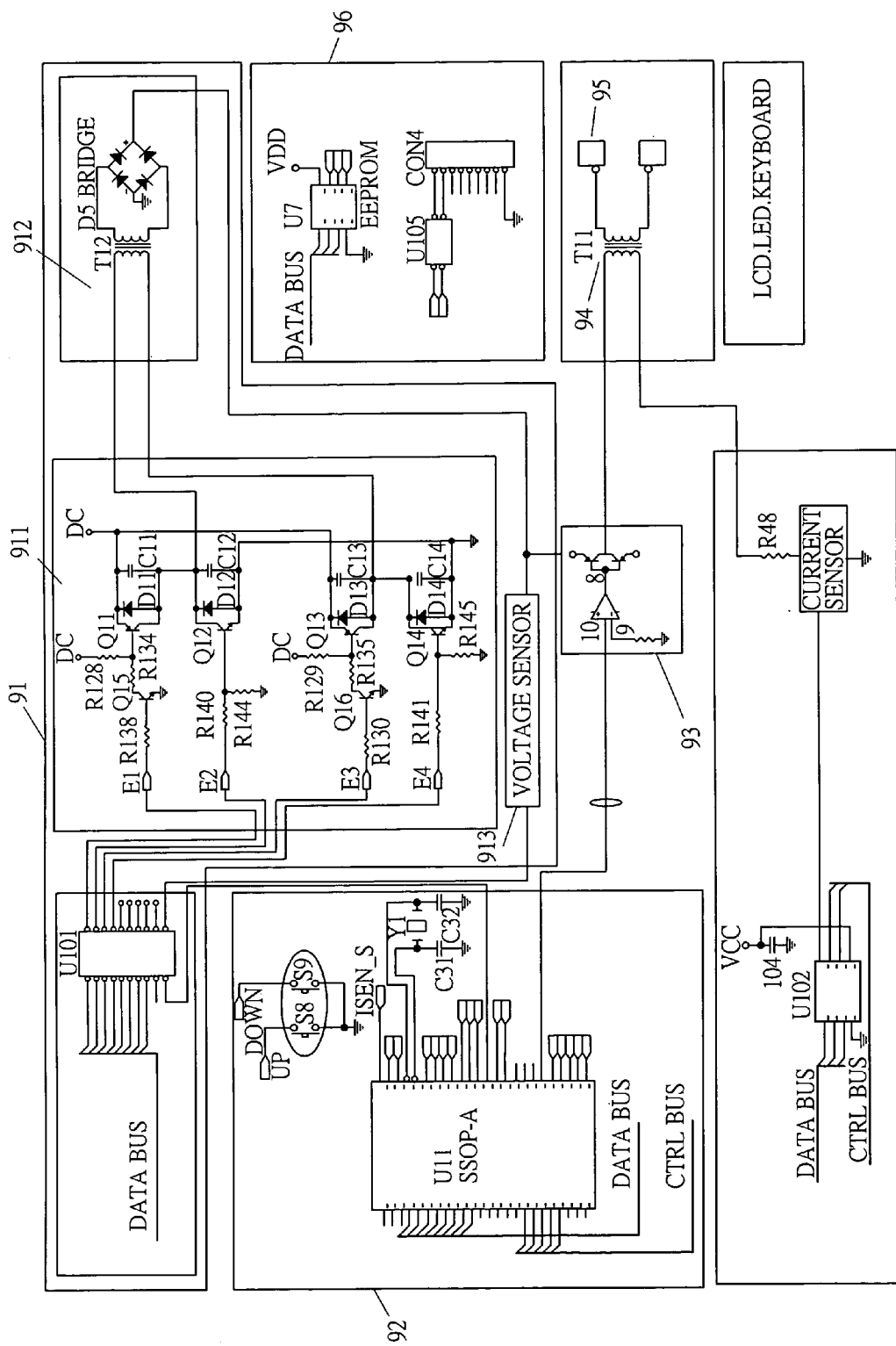
F I G. 7

FULL-RANGE ELECTROTHERAPY UNIT WITH DIGITAL FORCE MODUTATOR

BACKGROUND OF THE INVENTION

1. Field of the Invention

The present invention relates to an electrotherapy unit. In particular, the present invention relates to a full-range electrotherapy unit with a digital force modutator.

2. Description of the Related Art

Electrotherapy units comprise low frequency (lower than 1 kHz) types, medium frequency (1 kHz–5 kHz) types, and high frequency (above 5 kHz) types. The electrotherapy units include conductive pads to be in contact with the skin of a person receiving electric therapy by means of outputting low-frequency, medium-frequency, or high-frequency voltage to provide the human body with an electric stimulating effect.

FIG. 8 of the drawings illustrates a conventional electrotherapy unit comprising an analog power supply 10', an AM signal generator 20', an FM signal generator 30', an analog signal mixer 40', an analog power amplifier 50', a voltage-increasing transformer 60', and two conductive pads 70'. The analog power supply 10' supplies power to the analog power amplifier 50'. Input signals from the AM signal generator 20' or the FM signal generator 30' are inputted to the analog signal mixer 40' to create a medium-frequency vibrating voltage which is amplified by the analog power amplifier 50' and then increased by the voltage-increasing transformer 60'. An amplified AM or FM medium-frequency voltage is generated and outputted through the conductive pads 70' to provide the human body with an electric stimulating effect.

The analog power amplifier 50' is substantially an amplifying circuit consisting of an operational amplifier and two power transistors for amplifying the inputted voltage. The collector of each power transistor is connected to a primary coil of the voltage-increasing transformer 60'. However, the rectilinear analog power amplifier 50' has a relatively large power loss due to the temperature of the transistors, setting of the transistors, VCE voltage, current leakage, etc. Further, the electric circuit is apt to consume larger power and fails to provide a stable frequency under high frequency, as high-frequency parasitical oscillation is apt to be generated by a parasitical capacitor in the transistor. As a result, the electrotherapy unit could not be used in high frequency.

Further, since the collector of each transistor is connected to the primary coil of the voltage-increasing transformer that has an inductance, the reverse electromotive generated by the primary coil during reversion of the voltage would directly flow into the transistor, resulting in damage to the transistors.

SUMMARY OF THE INVENTION

An objective of the present invention is to provide an electrotherapy unit with a low loss and improved output efficiency.

Another objective of the present invention is to provide an electrotherapy unit that can be used throughout the full range of frequency.

A further objective of the present invention is to provide a stable electrotherapy unit.

Still another objective of the present invention is to provide an electrotherapy unit that can be downloaded with programs.

Yet another objective of the present invention is to provide a frequency-changeable electrotherapy unit.

In accordance with an aspect of the present invention, an electrotherapy unit comprises a digital force modutator, a power supply connected the digital force modutator and supplying power to the digital force modutator, a central processor connected to the digital force modutator, a voltage-increasing transformer including a primary coil and a secondary coil, and two conductive pads connected to the secondary coil.

The central processor is downloadable with programs to output signals for controlling operation of the digital force modutator. The digital force modutator comprises two pairs of transistors. Each transistor includes an input side connected to the central processor. The central processor controls conduction/non-conduction of the transistors. A loop for each transistor is connected to the power supply and the primary coil of the voltage-increasing transformer. A diode and a capacitor are connected in parallel between a collector and an emitter of each transistor. The diodes avoid damage to the transistors resulting from an electromotive generated by the primary coil of the voltage-increasing transformer. The capacitors reduce noise signals generated during switching operation of the transistors and the diodes. The capacitors provide bypass for high-frequency noise signals.

The electrotherapy unit may further comprise an interface circuit connected to the central processor. The interface circuit is connected to a computer and includes a non-volatile read-only memory.

In an embodiment, the power supply comprises an additional digital force modutator including an input end connected to the central processor and an output end connected to a power source end of the digital force modutator. The electrotherapy unit further comprises a rectifying transformer connected to the output end of the additional digital force modutator. Output power of the additional digital force modutator is controlled by the programs of the central processor.

The electrotherapy unit may further comprise a current sensor connected to the central processor. The central processor provides a feedback to compensate or to stop therapy when the current sensor detects abnormal current of the digital force modutator.

In accordance with another aspect of the invention, an electrotherapy unit comprises an analog power amplifier, a power supply connected the analog power amplifier and supplying power to the analog power amplifier, a voltage-increasing transformer, and two conductive pads connected to the voltage-increasing transformer. The power supply includes a digital force modutator and a rectifying transformer. A central processor is connected to the power supply and the analog power amplifier. The central processor is downloadable with programs to output signals for controlling operation of the digital force modutator and to output pulse signals to the analog power amplifier.

The digital force modutator comprises two pairs of transistors. Each transistor includes an input side connected to the central processor via an encoder. The central processor controls conduction/non-conduction of the transistors. A loop for each transistor is connected to the power supply and a primary coil of the rectifying transformer. The rectifying transformer includes an output connected to the analog power amplifier. A diode and a capacitor are connected in parallel between a collector and an emitter of each said transistor. The diodes avoid damage to the transistors resulting from an electromotive generated by the primary coil of the voltage-increasing transformer. The capacitors reduce noise signals generated during switching operation of the transistors and the diodes. The capacitors provide bypass for high-frequency noise signals.

The electrotherapy unit may further comprise a voltage sensor. The central processor provides a feedback to compensate or to stop therapy when the voltage sensor detects abnormal voltage.

Other objectives, advantages, and novel features of the invention will become more apparent from the following detailed description when taken in conjunction with the accompanying drawings.

BRIEF DESCRIPTION OF THE DRAWINGS

FIG. 5A is a schematic view illustrating waveforms outputted by the emitter of the transistor in an FM mode.

FIG. 5B is a schematic view illustrating waveforms outputted by the conductive pad in an FM mode.

FIG. 7 is a schematic circuitry diagram of another modified embodiment of the electrotherapy unit in accordance with the present invention.

DETAILED DESCRIPTION OF THE PREFERRED EMBODIMENTS

Figure 1:
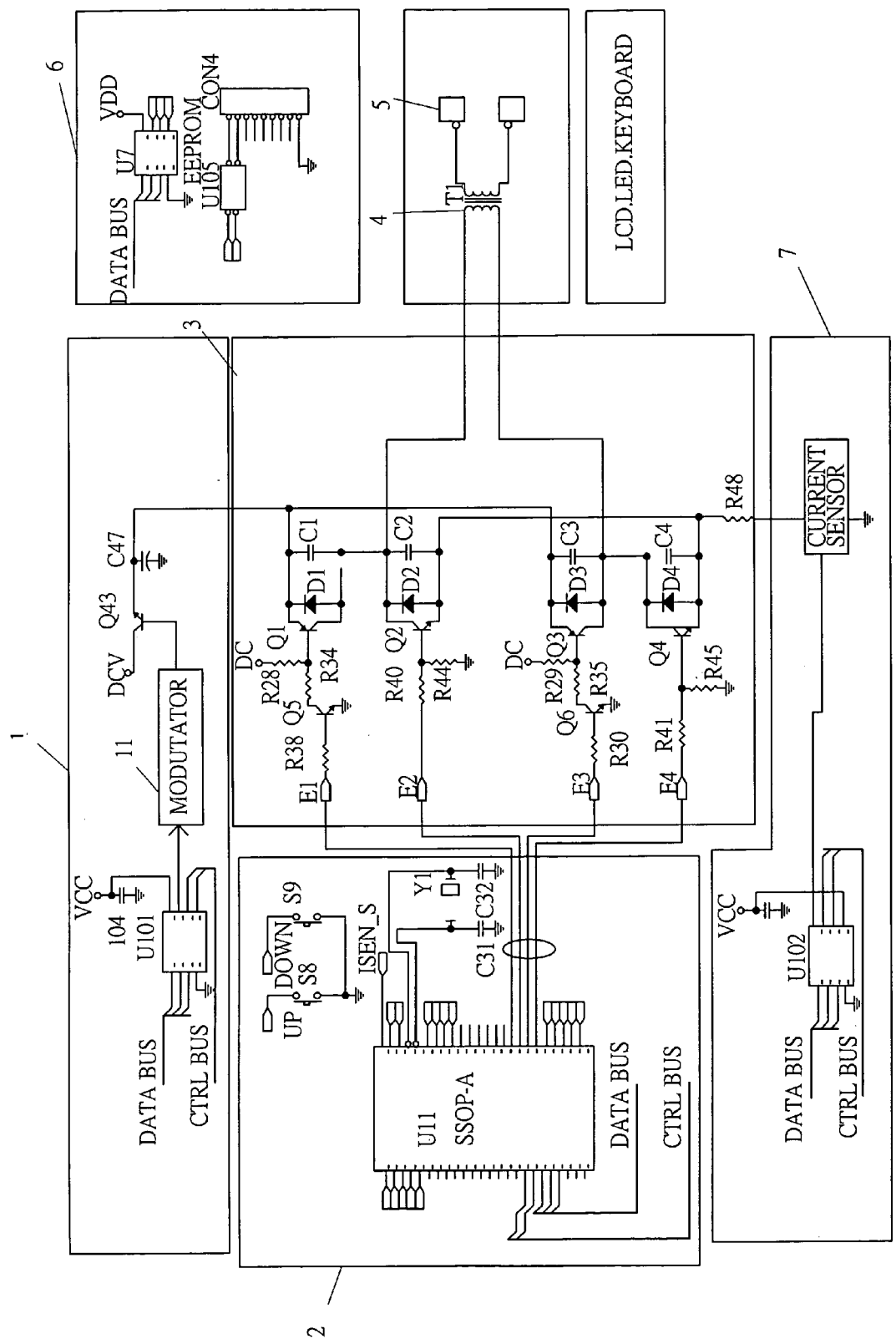
FIG. 1 is a circuitry diagram of an electrotherapy unit in accordance with the present invention.

Referring to FIG. 1, an electrotherapy unit in accordance with the present invention comprises a power supply 1, a central processor 2, a digital force modutator 3, a voltage-increasing transformer 4, two conductive pads 5, an interface circuit 6, and a current sensor 7.

The power supply 1 is connected to the central processor 2 and includes a U101DA converter that has an output connected to an analog modutator 11, a transistor Q43, and the digital force modutator 3. The central processor 2 controls signals inputted to the U 101 DA converter. Electric power outputted by the emitter of the transistor Q43 empowers the digital force modutator 3 under the control of the central processor 2.

The central processor 2 is connected to the power supply 1 and the digital force modutator 3. The central processor 2 can be programmed to output signals for controlling operation of the power supply 1 and the digital force modutator 3.

The digital force modutator 3 includes two pairs of transistors Q1, Q2, Q3, and Q4 to form a digital switch providing a modulating effect. The base of each of the transistors Q1 and Q3 is connected to a transistor Q5, Q6. The input side of the base of each transistor Q1, Q2, Q3, Q4 is connected to the central processor 2 that controls conductive/non-conductive state of the transistors Q1, Q2, Q3, and Q4. The loop of each transistor Q1, Q2, Q3, Q4 is connected to the power supply 1 and the primary coil of the voltage-increasing transformer 4. A diode D1, D2, D3, D4 and a capacitor C1, C2, C3, C4 are connected in parallel between the collector and the emitter of each transistor Q1, Q2, Q3, Q4. Preferably, the transistors Q1 and Q3 are PNP transistors and the transistors Q2 and Q4 are NPN transistors.

The voltage-increasing transformer 4 includes a secondary coil connected to the conductive pads 5. The voltage-increasing transformer 4 increases the voltage of the primary coil to create an appropriate voltage for the conductive pads 5.

The interface circuit 6 includes a non-volatile read-only memory (EEPROM) U7 and a communication interface U105 (RS485). The interface circuit 6 may be connected to a computer to modify programs in the central processor 2 or to downward programs to the central processor 2.

The current sensor 7 is connected to the digital force modutator 3 and the central processor 2. The current sensor 7 is capable of detecting abnormal current of the digital force modutator 3. In response to the abnormal current, the central processor 2 provides an appropriate feedback to compensate or to stop therapy, providing a stabilizing function.

Figure 2A:
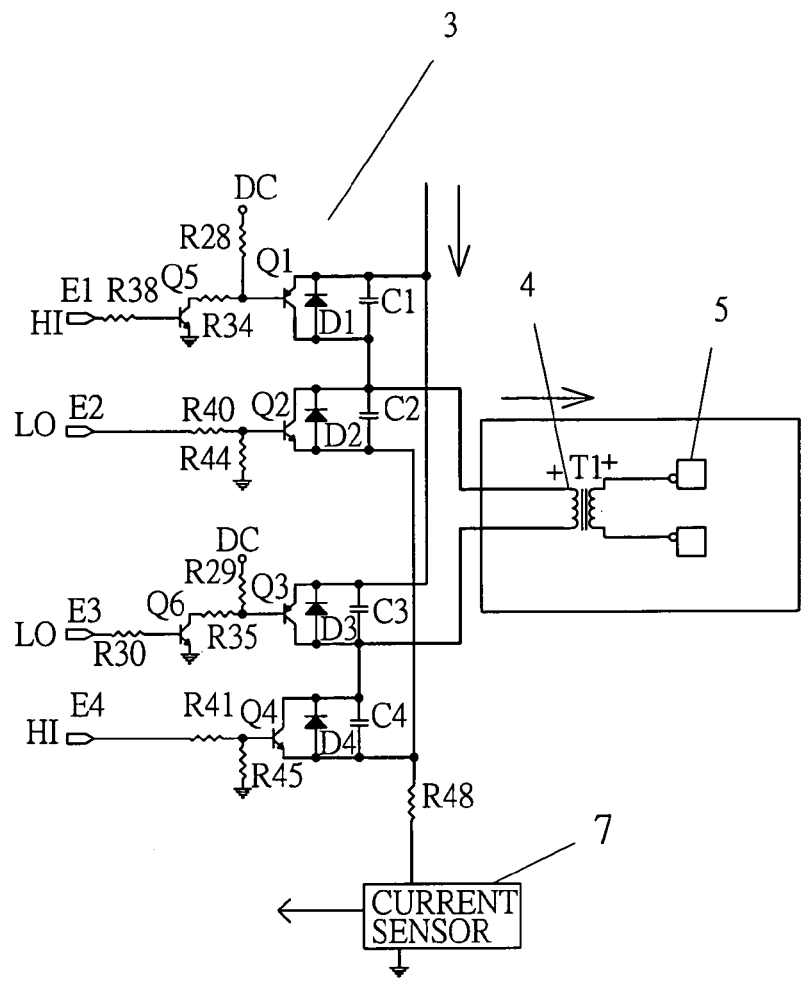
FIG. 2A is a schematic view illustrating operation of a positive half cycle of a digital force modutator of the electrotherapy unit in accordance with the present invention.
Figure 2B:
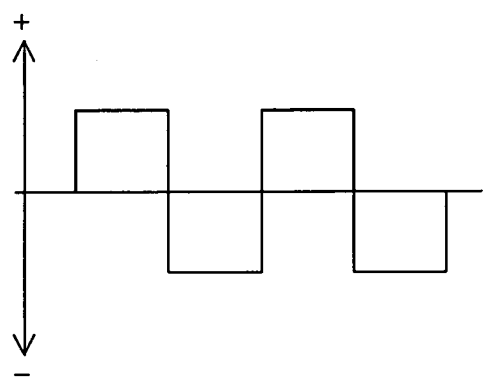
FIG. 2B is a schematic view illustrating waveforms outputted during the positive half cycle of the digital force modutator of the electrotherapy unit in accordance with the present invention.

Referring to FIGS. 2A and 2B, during a positive half cycle, the central processor 2 sends Hi signals to the transistors Q1 and Q4 to make the transistors Q1, Q4, and Q5 conductive. The bold lines in FIG. 2A indicate the flowing direction of current. As a result, the primary coil of the voltage-increasing transformer 4 generates a positive half cycle voltage. Meanwhile, the central processor 2 sends Lo signals to the transistors Q2 and Q3 to make the transistors Q2, Q3, and Q6 non-conductive.

Figure 3A:
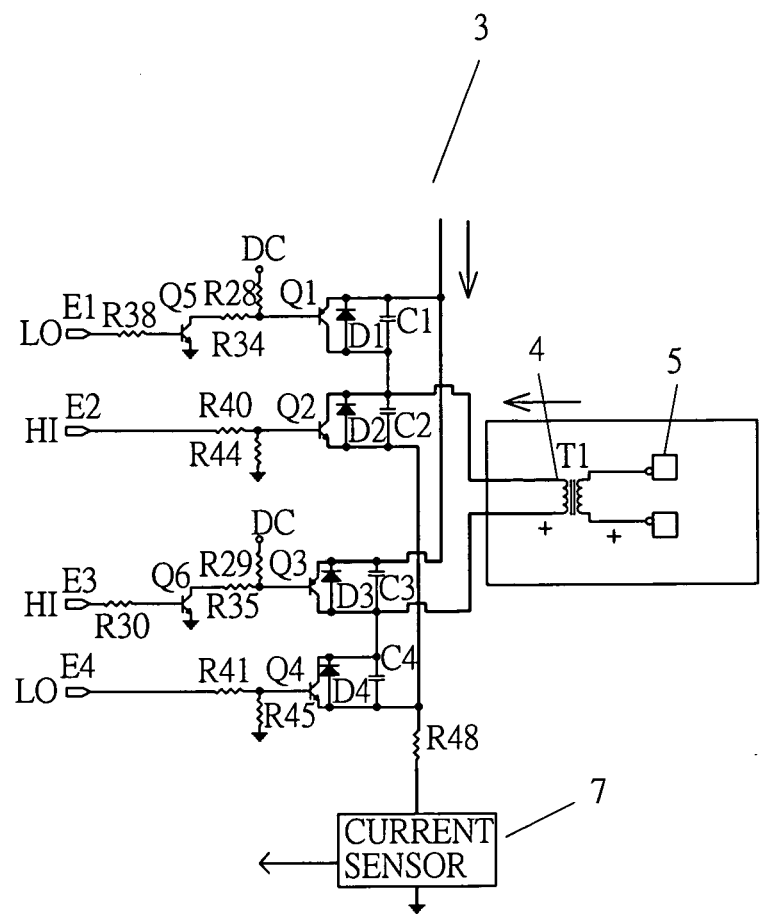
FIG. 3A is a schematic view illustrating operation of a negative half cycle of the digital force modutator of the electrotherapy unit in accordance with the present invention.
Figure 3B:
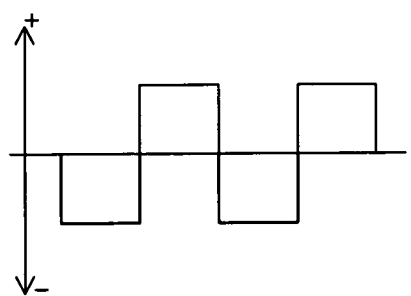
FIG. 3B is a schematic view illustrating waveforms outputted during the negative half cycle of the digital force modutator of the electrotherapy unit in accordance with the present invention.

Referring to FIGS. 3A and 3B, during a negative half cycle, the central processor 2 sends Hi signals to the transistors Q2, Q3, and Q6 to make the transistors Q2 and Q3 conductive. The bold lines in FIG. 3A indicate the flowing direction of current. As a result, the primary coil of the voltage-increasing transformer 4 generates a negative half cycle voltage. Meanwhile, the central processor 2 sends Lo signals to the transistors Q1 and Q4 to make the transistors Q1, Q4, and Q5 non-conductive. Thus, the conduction/non-conduction of the transistors Q1, Q2, Q3, and Q4 can be controlled by programs to control output of positive/negative oscillating voltage.

Since a diode D1, D2, D3, D4 is connected in parallel between the collector and the emitter of each transistor Q1, Q2, Q3, Q4, the voltage between the collector and the emitter of each transistor Q1, Q2, Q3, Q4 is controlled in a range between −0.6 V and +0.6 V (the input power voltage). When the primary coil of the voltage-increasing transformer 4 generates a reverse electromotive due to a change in the input voltage, the diodes D1, D2, D3, and D4 allow bypassing of the reverse electromotive to prevent damage to the transistors Q1, Q2, Q3, and Q4.

Since a capacitor C1, C2, C3, C4 is connected in parallel between the collector and the emitter of each transistor Q1, Q2, Q3, Q4 and connected in parallel with the diode D1, D2, D3, D4, the noise signals resulting from the switching actions of the transistors Q1, Q2, Q3, and Q4 and the diodes D1, D2, D3, and D4 can be lowered. Further, since the capacitor C1, C2, C3, C4 has a capacitance smaller than the potential capacitance of the transistors Q1, Q2, Q3, and Q4, the diodes D1, D2, D3, and D4, and the primary coil of the voltage-increasing transformer 4, high-frequency noise signals can be bypassed through the capacitors C1, C2, C3, and C4, and a rise of temperature of the transistors Q1, Q2, Q3, and Q4 resulting from high-frequency noise signals is prevented.

Thus, the programs of the central processor 2 control conduction and non-conduction of the transistors Q1, Q2, Q3, and Q4 of the digital force modutator 3, and the central processor 2 cooperates with the diodes D1, D2, D3, and D4 and the capacitors C1, C2, C3, and C4 to provide a near-zero voltage switching function while improving the efficiency of the electrotherapy unit. Thus, the electrotherapy unit in accordance with the present invention can be used throughout the full range of frequency (i.e., low-frequency, medium frequency, and high-frequency).

Figure 4A:
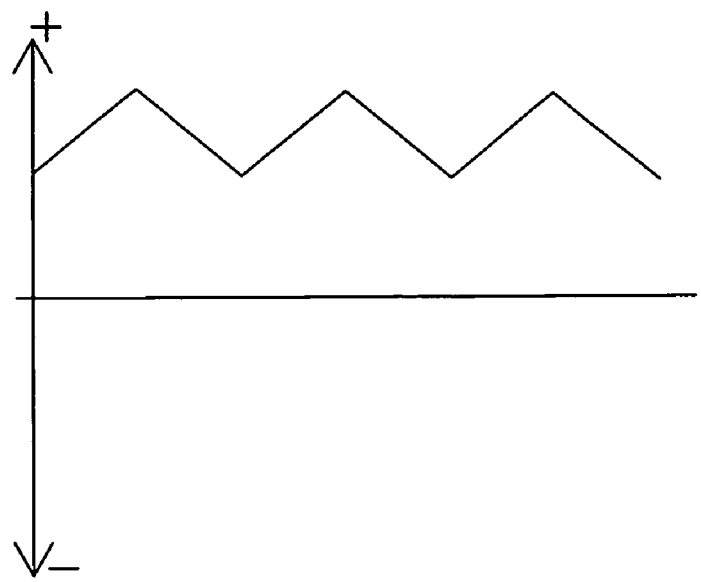
FIG. 4B is a schematic view illustrating waveforms outputted by a conductive pad in an AM mode.
Figure 4B:
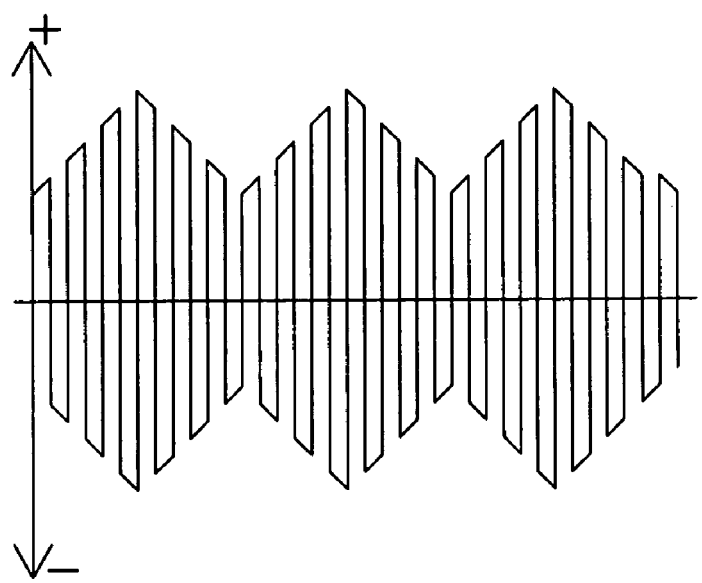

When the power supply 1 is in an AM mode, the waveforms outputted by the emitter of the transistor Q43 are AM amplitude-modulated waveforms (FIG. 4A). The AM waveforms are inputted into the digital force modutator 3, and the conductive pads 5 generate positive/negative amplitude-modulated voltage waveforms in AM mode (FIG. 4B) to provide electric therapy in AM mode.

On the other hand, when the power supply 1 is in an FM mode, the waveforms outputted by the emitter of the transistor Q43 are horizontal (FIG. 5A). The FM waveforms are inputted into the digital force modutator 3, and the conductive pads 5 generate positive/negative amplitude-modulated voltage waveforms in FM mode (FIG. 5B) to provide electric therapy in FM mode.

Thus, the digital force modulator 3 of the electrotherpy unit cooperates with the power outputt by the power supply 1 to obtain modulated output with an improved efficiency, allowing the user to select electric therpy between AM mode and FM mode.

The interface circuit 6 provides a connection of the electrotherapy unit to a computer. Thus, programs can be downloaded to the central processor 2 in response to different needs. Further, the programs in the central processor 2 can be modified by remote control through Internet, allowing medical personnel to set electric therapy programs for a remote user receiving electric therapy.

Figure 6:
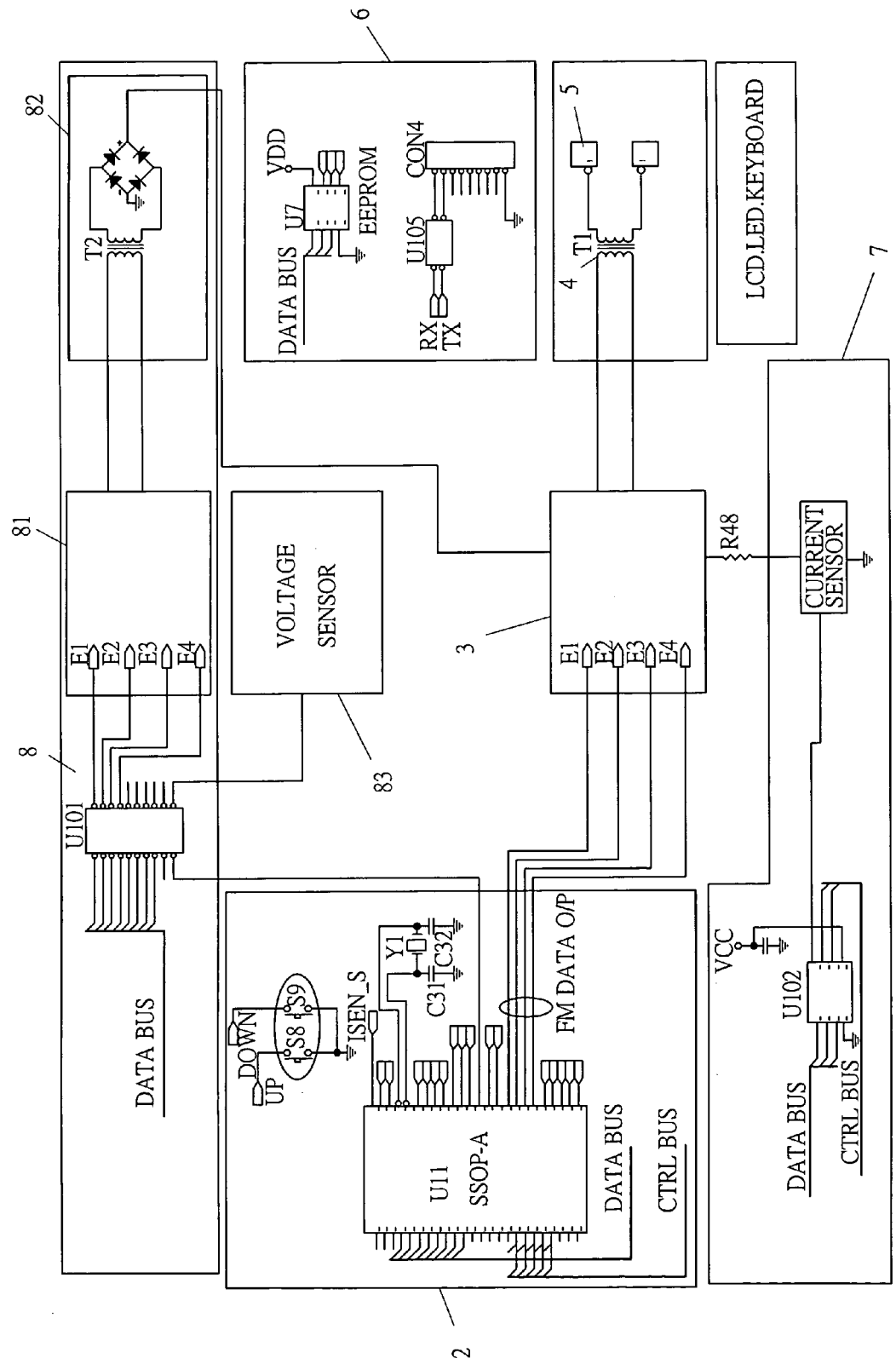
FIG. 6 is a schematic circuitry diagram of a modified embodiment of the electrotherapy unit in accordance with the present invention.
Figure 8:
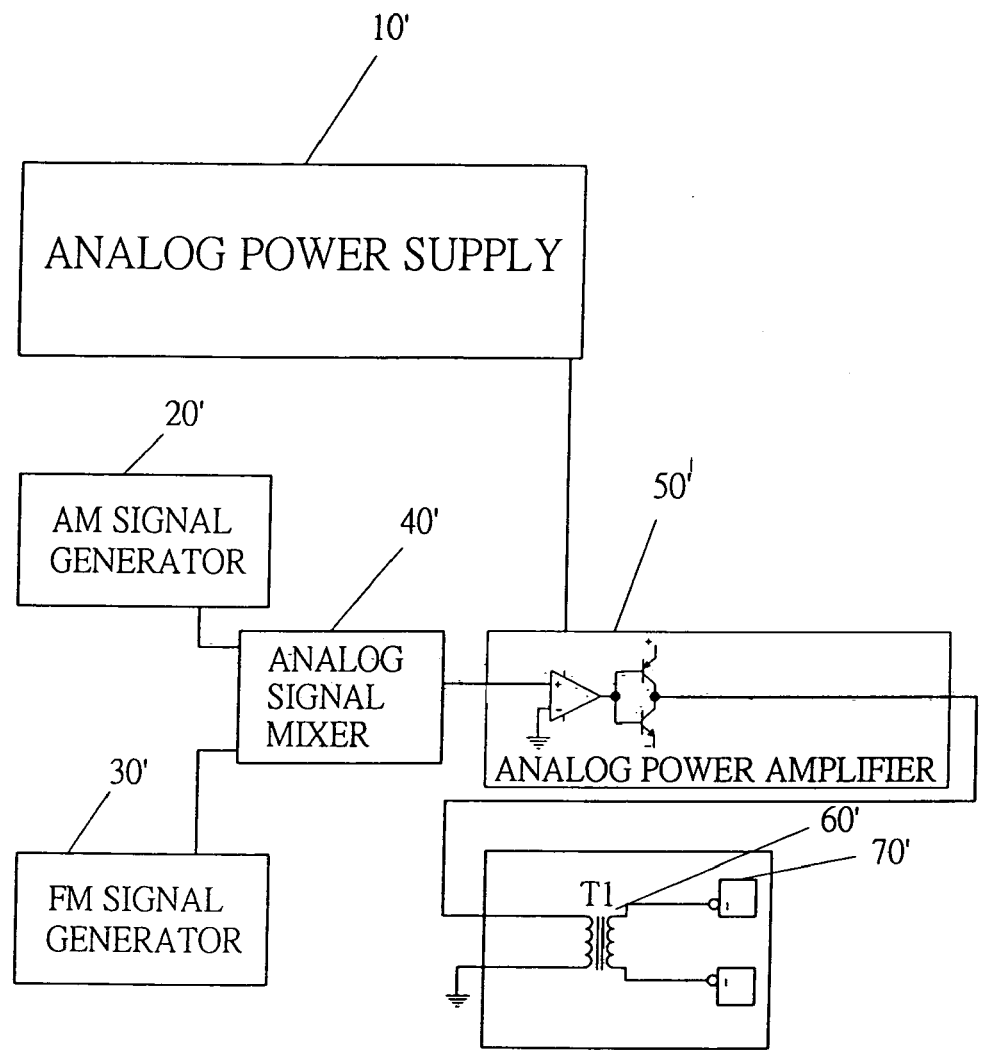
FIG. 8 is a schematic block diagram of a conventional electrotherapy unit.

FIG. 6 illustrates a modified embodiment of the electrotherapy unit. In this embodiment, the electrotherapy unit comprises a power supply 8 and a digital force modutator 81 that is substantially the same as the digital force modutator 3. An input end of the digital force modutator 81 is connected to an encoder U101 that is connected to the central processor 2. An output end of the digital force modutator 81 is connected to a rectifying transformer 82, which, in turn, is connected to the power source end of the digital force modutator 3 that controls the conductive pads 5. The digital force modutator 81 includes a frequency-modulating function or pulse-width modulating function to control output voltage through the programs of the central processor 2, forming a digital power supply. The output power is higher and the loss is reduced as compared to a conventional analog type. Thus, the overall efficiency of the electrotherapy unit can be further improved. Further, the power supply 8 includes a voltage sensor 83 to provide a feedback or to stop therapy when abnormal voltage is detected, providing a stabilized operation.

FIG. 7 illustrates another modified embodiment of the electrotherapy unit in accordance with the present invention. In this embodiment, the electrotherapy unit comprises a power supply 91, a central processor 92, an analog power amplifier 93, a voltage-increasing transformer 94, two conductive pads 95, an interface circuit 96, and a current sensor 97.

The power supply 91 includes a digital force modutator 911 that has an input end connected to the central processor 92 and that has an output end connected to a rectifying transformer 912 and the analog power amplifier 93. The digital force modutator 911 includes two pairs of transistors Q11, Q14 and Q12, Q13, which is substantially the same as that of the above-mentioned digital force modutator 3. The base of each of the transistors Q11 and Q13 is connected to a transistor Q15, Q16. The input side of the base of each transistor Q11, Q12, Q13, Q14 is connected to the central processor 92 that controls conductive/non-conductive state of the transistors Q11, Q12, Q13, and Q14. The loop of each transistor Q11, Q12, Q13, Q14 is connected to the primary coil of a transformer 914 of the rectifying transformer 912. A diode D11, D12, D13, D14 and a capacitor C11, C12, C13, C14 are connected in parallel between the collector and the emitter of each transistor Q11, Q12, Q13, Q14. Preferably, the transistors Q11 and Q13 are PNP transistors and the transistors Q12 and Q14 are NPN transistors. The power supply 91 includes a voltage sensor 913 to provide a feedback or to stop therapy through control of the central processor 92 when abnormal voltage is detected.

The central processor 92 is connected to the power supply 91 and the analog power amplifier 93. Programs can be downloaded to the central processor 92 to control activation of the power supply 91 and to output pulse signals for controlling operation of the analog power amplifier 93.

Thus, the programs of the central processor 92 control conduction and non-conduction of the transistors Q11, Q12, Q13, and Q14 of the digital force modutator 911, and the central processor 92 cooperates with the diodes D11, D12, D13, and D14 and the capacitors C11, C12, C13, and C14 to improve the efficiency of power inputted to the analog power amplifier 93. Further, the digital force modutator 911 in the power supply 91 cooperates with the analog power amplifier 93 to provide improved efficiency as compared to the conventional electrotherapy units.

Although specific embodiments have been illustrated and described, numerous modifications and variations are still possible without departing from the essence of the invention. The scope of the invention is limited by the accompanying claims.

What is claimed is:

1. An electrotherapy unit comprising:
   a digital force modutator;
   a power supply connected to the digital force modutator and supplying power to the digital force modutator;
   a central processor connected to the digital force modutator, the central processor being downloadable with programs to output signals for controlling operation of the digital force modutator;
   a voltage-increasing transformer including a primary coil and a secondary coil; and
   two conductive pads connected to the secondary coil;
   the digital force modutator comprising two pairs of transistors, each said transistor including an input side connected to the central processor, the central processor controlling conduction/non-conduction of the transistors, a loop for each said transistor being connected to the power supply and the primary coil of the voltage-increasing transformer, a diode and a capacitor being connected in parallel between a collector and an emitter of each said transistor;

wherein the voltage-increasing transformer, one of the transistor, one of the diodes connected to said one of the transistors, and one of the capacitors connected to said one of the transistors together form a loop for providing a near-zero voltage switching function.

2. The electrotherapy unit as claimed in claim 1, wherein the power supply comprising an additional digital force modutator including an input end connected to the central processor and an output end connected to a power source end of the digital force modutator, the electrotherapy unit further comprising a rectifying transformer connected to the output end of said additional digital force modutator, output power of said additional digital force modutator being controlled by the programs of the central processor.

3. The electrotherapy unit as claimed in claim 1, wherein the electrotherapy unit further comprises a current sensor connected to the central processor, the central processor providing a feedback to compensate or to stop therapy when the current sensor detects abnormal current of the digital force modutator.

4. An electrotherapy unit comprising:
  an analog power amplifier;
  a power supply connected to the analog power amplifier and supplying power to the analog power amplifier, the power supply including a digital force modutator and a rectifying transformer;
  a central processor connected to the power supply and the analog power amplifier, the central processor being downloadable with programs to output signals for controlling operation of the digital force modutator and to output pulse signals to the analog power amplifier;
  a voltage-increasing transformer; and
  two conductive pads connected to the voltage-increasing transformer;
  the digital force modutator comprising two pairs of transistors, each said transistor including an input side connected to the central processor via an encoder, the central processor controlling conduction/non-conduction of the transistors, a loop for each said transistor being connected to the power supply and a primary coil of the rectifying transformer, the rectifying transformer including an output connected to the analog power amplifier, a diode and a capacitor being connected in parallel between a collector and an emitter of each said transistor;
  wherein the voltage-increasing transformer, one of the transistors, one of the diodes connected to said one of the transistors, and one of the capacitors connected to said one of the transistors together form a loop for providing a near-zero voltage switching function.

5. The electrotherapy unit as claimed in claim 4, wherein the electrotherapy unit further comprises a voltage sensor, the central processor providing a feedback to compensate or to stop therapy when the voltage sensor detects abnormal voltage.

* * * * *